United States Patent
Schmitt-Manderbach et al.

(10) Patent No.: US 8,965,065 B2
(45) Date of Patent: Feb. 24, 2015

(54) METHOD AND DEVICE FOR DETERMINING VARIOUS BIOMETRIC PARAMETERS OF AN EYE BY INTERFEROMETRY

(75) Inventors: Tobias Schmitt-Manderbach, Jena (DE); Daniel Bublitz, Rausdorf (DE); Roland Bergner, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 139 days.

(21) Appl. No.: 13/876,779

(22) PCT Filed: Sep. 15, 2011

(86) PCT No.: PCT/EP2011/065999
§ 371 (c)(1),
(2), (4) Date: Mar. 28, 2013

(87) PCT Pub. No.: WO2012/041712
PCT Pub. Date: Apr. 5, 2012

(65) Prior Publication Data
US 2013/0188843 A1 Jul. 25, 2013

(30) Foreign Application Priority Data
Sep. 29, 2010 (DE) .......................... 10 2010 047 053

(51) Int. Cl.
*G06K 9/00* (2006.01)
*A61B 3/10* (2006.01)
(Continued)

(52) U.S. Cl.
CPC ............ *G06K 9/0061* (2013.01); *A61B 3/1005* (2013.01); *A61B 3/11* (2013.01); *G01B 11/00* (2013.01); *G01B 9/02091* (2013.01); *A61B 3/113* (2013.01)
USPC ............................ 382/117; 382/131; 351/221

(58) Field of Classification Search
CPC .......... G06K 9/00597; G06K 9/00604; G06K 9/0061; G06K 9/00476; G06T 2207/30216; G06T 7/408; G06T 17/05
USPC .................................... 382/117, 131; 351/221
See application file for complete search history.

(56) References Cited

U.S. PATENT DOCUMENTS 5,889,577 A   3/1999  Kohayakawa
6,779,891 B1  8/2004  Barth et al.
(Continued)

FOREIGN PATENT DOCUMENTS

DE   198 57 001 A1   6/2000
DE   101 08 797 A1   9/2002
(Continued)

OTHER PUBLICATIONS

Drexler, W. et al.; "Submicrometer Precision Biometry of the anterior Segment of the Human Eye"; Investigative Ophthalmology & Visual Science, vol. 38, No. 7, pp. 1034ff, 1997.

*Primary Examiner* — Ruiping Li
(74) *Attorney, Agent, or Firm* — Patterson Thuente Pedersen, P.A.

(57) ABSTRACT

Determination of biometric parameters of an eye, in which the optical axis of the biometric measurement system is aligned to the optical axis of an eye. The device includes an interferometry measuring arrangement having a measurement light source and a measurement sensor, a fixation light source for capturing the eye with the reflexes that arise, an image sensor, and lens for detecting volume scattered light and an analysis unit for determining the angular deviation of the optical axis of the eye from the optical axis of the biometric measurement system. The analysis unit compares determined angular deviation to a predefined tolerance and, laterally displaces fixation marks on the basis of the calculated angular deviation, or of initiating the biometric measurement.

18 Claims, 3 Drawing Sheets

(51) Int. Cl.
*A61B 3/11* (2006.01)
*G01B 11/00* (2006.01)
*G01B 9/02* (2006.01)
*A61B 3/113* (2006.01)

(56) References Cited

U.S. PATENT DOCUMENTS

| | | | |
|---|---|---|---|
| 7,380,939 B2 | 6/2008 | Barth et al. | |
| 2004/0070728 A1* | 4/2004 | Bergner et al. | 351/206 |
| 2005/0007551 A1 | 1/2005 | Wakil et al. | |
| 2005/0286019 A1 | 12/2005 | Wiltberger et al. | |

FOREIGN PATENT DOCUMENTS

| | | |
|---|---|---|
| DE | 103 49 230 A1 | 7/2005 |
| DE | 10 2008 051 272 A1 | 4/2010 |
| DE | 10 2009 007 732 A1 | 8/2010 |
| WO | WO 01/01064 A2 | 1/2001 |
| WO | WO 02/065899 A2 | 8/2002 |
| WO | WO 03/003909 A2 | 1/2003 |
| WO | WO 2004/103169 A2 | 12/2004 |
| WO | WO 2007/053971 A1 | 5/2007 |

* cited by examiner

METHOD AND DEVICE FOR DETERMINING VARIOUS BIOMETRIC PARAMETERS OF AN EYE BY INTERFEROMETRY

PRIORITY CLAIM

The present application is a National Phase entry of PCT Application No. PCT/EP2011/065999, filed Sep. 15, 2011, which claims priority from German Application No 10 2010 047 053.8, filed Sep. 29, 2010, the disclosures of which are hereby incorporated by reference herein in their entirety.

FIELD OF THE INVENTION

The present invention relates to a solution for interferometrically determining various biometric parameters of an eye, wherein the optical axis of the biometric measurement system is aligned with the optical axis of an eye and ideally coincides with said axis.

BACKGROUND

While the optical axis of the eye is characterized by the straight line between the centers of curvature of refractive surfaces, the axis that extends from the "fovea centralis" through the nodal point of the eye to the fixing object is designated as the visual axis. If the different media are mathematically reduced to a single medium with an average index of refraction and a spherical curvature, a point in the eye can be defined through which all beams pass without being refracted. This point is designated as nodal point of the visual axes.

Usually, in all eyes, the visual axis deviates from the optical axis. This results, on the one hand, from aberrations of the eye which, for example, are a result of the fact that curvature radii of the individual eye media are not uniform, the eye lens is tilted, the retina is not in the focus of the eye lens, and much more. On the other hand, when aligning the eye with an object, it is hereby attempted to image said object, whenever possible, in the fovea as the area of the sharpest vision.

While the alignment of the eye plays no role for many examinations in ophthalmology, at least the knowledge about the alignment of the eye relative to the ophthalmological device is absolutely necessary not only for the treatment of the eye but also for the measurement of the eye.

Determining different biometric parameters of an eye is necessary, in particular, prior to a surgical intervention for replacing the eye lens in the event of lens opacity (cataract). In order to ensure optimal vision after the surgery, it is necessary to determine these parameters with adequately high accuracy so as to be able to subsequently select a suitable replacement lens based on the determined measurements. The most important parameters to be determined are, among other things, the axial length (distance from the cornea to the retina), the corneal curvature and corneal refractive power, and the length of the anterior chamber (distance from the cornea to the eye lens).

Thus, for carrying out biometric measurements on the eye it is advantageous if the optical axis of the ophthalmological measuring arrangement and the optical axis of the eye to be measured are aligned with each other and ideally coincide. This ensures during biometric measurements according to the principle of the short-coherence interferometry that from the weak light portions reflected by the boundary surfaces of cornea and lens, sufficient signal intensity reaches the detector and generates a measurable interference contrast.

According to the known prior art, different solutions for interferometric determination of distances in the eye are known, each solution placing different high demands on the alignment of the eye with the ophthalmological device.

A first arrangement for interferometrically measuring the distances of the anterior eye segments is described by Drexler, W. et al. in [1]. For aligning the visual axis of the eye with the optical axis of the measuring arrangement, collimated fixing light is reflected along a fixed coaxial direction into the measuring beam path. Adjusting the angle between the visual axis of the patient and the optical axis of the measuring arrangement is carried out with the aid of a scanning mirror. For this, the alignment of the two axes has to be performed with an accuracy better than 1° because otherwise no overlapping of cornea reflex and lens reflex occurs on the detector and no analyzable interference signal arises. Accordingly, the sensitivity of the setup to tilting of the patient's eye is very high. Here, the position of the visual axis of the eye is determined by means of scanning over a predetermined angular range in two orthogonal spatial directions. The method described here is very time-consuming and, in addition, is not reliable enough in daily clinical practice.

Another solution for determining distances at the anterior eye segment, preferably the pupil and/or iris diameter, is described in DE 101 08 797 A1. Here too, the proband is offered a light mark on which he/she fixes his/her eye. During the entire time of adjusting and measuring, the user can visually monitor that the proband fixes correctly. In contrast to the schematic eye according to Gullstrand, in real eyes, the visual axis and the optical axis can deviate from each other by up to 8° since the fovea can be offset from 3° nasally to 8° temporally. Accordingly, it can be advantageous here to offer the proband an offset fixing light. As in the previously described solution, the alignment of both eyes with each other has to be carried out with high accuracy. This is of particular importance here since during the determination of pupil and/or iris diameters, not scattered light but reflected light is detected.

A significantly improved method is described in U.S. Pat. No. 7,380,939. Here, instead of a cost-intense scanning mirror, fixing light generated by an LC display is used. Said fixing light is not only variably adjustable in terms of its lateral position but also in terms of its apparent distance from the patient's eye so as to take account of a potential defective vision of the patient.

In addition, through intentionally defocussing the measuring beam by means of axial displacement of the focusing lens relative to the patient's eye, cornea reflexes and lens reflexes are imaged on the detector in an unsharp and enlarged manner. Through this, the sensitivity of the measuring arrangement to tilting or lateral displacement of the patient's eye is slightly reduced.

However, the disadvantage is that due to the use of a dual beam interferometer, the measuring light portions reflected by different boundary surfaces in the eye generate the interference signal; thus, no external reference light serves for generating the interference contrast. For this reason, only non-diffraction-limited imaging of the reflected light on the photo detector can be selected so that only specular (Fresnel) reflexes contribute to the interference signal. The speckles caused by volume scattered light are significantly smaller in the detector plane than the detector area and are therefore "averaged out" over the detector area. As a result of this, the measurement method continues to be dependent on a generally very precise pre-adjustment to the visual axis of the patient's eye.

A third technical solution known from the documents WO 2001/38820A1 and WO 0207/053971A1 uses a diffraction-limited capture of the measuring light scattered back in the eye for interferometrically determining distances in the eye; however, this solution has only one fixing light fixedly positioned on the optical axis of the measuring arrangement. Thus, with this arrangement, a variable fixing of the viewing direction, which is advantageous for the measurement, cannot be achieved.

Literature:

[1] Drexler, W. et al.; "Submicrometer Precision Biometry of the anterior Segment of the Human Eye"; Investigative Ophthalmology & Visual Science, Vol. 38, No. 7, pages 1034ff

SUMMARY OF THE INVENTION

Findings from practice have surprisingly shown that near the so-called glancing angle, increased intensity of backscattering occurs. Although in the case of a diffraction-limited detection the generated volume scattered light is utilized, which substantially uniformly remits in all directions, an at least rough pre-adjustment of the optical axis of the ophthalmological measurement device with regard to the visual axis would result in considerably improved measurement results.

In this connection, FIG. 1 shows the intensity curve of the light portions scattered back by a boundary surface in the eye as a function of the scattering angle. It is shown that the backscattered light portions have a significantly higher intensity in a narrow range around the so-called glancing angle than in the remaining range.

It is therefore an object of the present invention to develop a solution for interferometrically determining various biometric parameters of an eye, which solution delivers accurate and reliable measured values but nevertheless is not dependent on a highly accurate alignment of the device with the eye of a patient. Here, a sufficiently accurate alignment of the optical axis of an interferometric measuring arrangement with regard to the optical axis of an eye shall preferably be carried out automatically, wherein tilting or lateral displacements of the patient's eye and also the defective vision thereof shall be considered during the alignment.

According to the invention, this object is achieved by the features of the independent claims. Preferred refinements and configurations are subject matter of dependent claims.

With the method according to the invention for interferometrically determining various biometric parameters of an eye, wherein the eye is illuminated by a measuring light source with a measuring beam and by a fixing light source with a fixing mark, the eye is captured by an image sensor with the reflexes that arise, and from the position of the reflexes with regard to the center of the pupil or the iris, the angular deviation of the optical axis of the eye from the optical axis of the biometric measuring system is determined by an analysis unit, the object is achieved in that prior to the determination of the various biometric parameters, the alignment of the biometric measuring system is carried out, in that A) for refixing purposes, the eye is illuminated by the fixing light source with a laterally displaced fixing mark based on the calculated angular deviation, B) the eye is captured by the image sensor with the reflexes that arise, C) from the position of the reflexes with regard to the center of the pupil or the iris, the angular deviation of the optical axis of the eye from the optical axis of the ophthalmological device is determined by the analysis unit, D) the determined angular deviation is compared by the analysis unit with a predefined tolerance, and E) the method steps A) to D) are repeated if the determined angular deviation exceeds a predefined tolerance.

Otherwise, determining various biometric parameters of an eye is carried out in that F) the measuring light reflected by the eye is detected in the form of volume scattered light, G) is superimposed as a quasi-diffraction-limited measuring beam with an external reference beam, is directed onto the measurement sensor, and H) the interferometric measurement signals are analyzed by the analysis unit.

With the device according to the invention for interferometrically determining various biometric parameters of an eye, said device consisting of an interferometric measuring arrangement, a measuring light source for illuminating an eye with measuring light, a fixing light source for illuminating the eye with a fixing mark, an image sensor for capturing the eye with the reflexes that arise, and an analysis unit for determining the angular deviation of the optical axis of the eye from the optical axis of the biometric measurement system, the object is achieved in that the fixing light source is designed in such a manner that the fixing mark to be generated is laterally displaceable, an existing lens is designed in such a manner that primarily volume scattered light is detected, the interferometric measuring arrangement is designed for superimposing the measuring light with external reference light, and the analysis unit is capable of comparing the determined angular deviation with a predefined tolerance and, for the purpose of refixing as a result of said comparison, makes the fixing light source generate a laterally displaced fixing mark on the basis of the calculated angular deviation, or initiates the biometric measurement.

Although the proposed technical solution is primarily intended for ophthalmological devices for biometrically measuring the distances and radii in the eye, said solution can principally also be used for other devices in ophthalmology.

BRIEF DESCRIPTION OF THE DRAWINGS

The invention is described in more detail hereinafter by means of exemplary embodiments. In the figures.

DETAILED DESCRIPTION

With the method according to the invention for interferometrically determining various biometric parameters of an eye, the eye is illuminated by a measuring light source with a measuring beam and by a fixing light source with a fixing mark, is captured by an image sensor with the reflexes that arise, and from the position of the reflexes with regard to the center of the pupil or the iris, the angular deviation of the optical axis of the eye from the optical axis of the biometric measurement system is determined by an analysis unit. While the fixing light source is bound to emit light in the visible spectral range, the measuring light source emits a measuring beam in a spectral range that is not visible for the patient, which simplifies the analysis of the captured images significantly.

Prior to determining the various biometric parameters, the alignment of the biometric measurement system is carried out in that in a first method step A) for refixing the fixing light source based on the calculated angular deviation, the eye is illuminated with a laterally displaced fixing mark, and in the next method step B), the eye is captured by the image sensor with the reflexes that arise.

In a further method step C), from the position of the reflexes with regard to the center of the pupil or the iris, the angular deviation of the optical axis of the eye from the optical axis of the biometric measurement system is determined by the analysis unit, and according to method step D), is compared by the analysis unit with a predefined tolerance. In the method step E), as a result of this comparison, the repetition of the method steps A) to D) is initiated if the determined angular deviation exceeds a predefined tolerance. Here, the alignment of the optical axis of the eye with the optical axis of the biometric measurement system is performed by specifically changing the visual axis of the eye through a corrected fixing mark.

Otherwise, determining various biometric parameters of an eye is carried out in that in a further method step F), the measuring light reflected by the eye is detected in the form of volume scattered light and in the method step G), is superimposed as a diffraction-limited measuring beam with an external reference beam and is directed onto the measuring sensor, and in the last method step H), the interferometric measurement signals are analyzed by the analysis unit.

In this manner, the biometric measurement system is optimized for the physiology of the patient prior to the actual interferometric measurement for determining the position of optical boundary surfaces in the eye. This is preferably carried out automatically by the proposed solution, wherein the calculation and activation of the fixing mark that is laterally displaced by the fixing light source is carried out in the described manner, thus, automatically and without involvement of the user.

Figure 1:
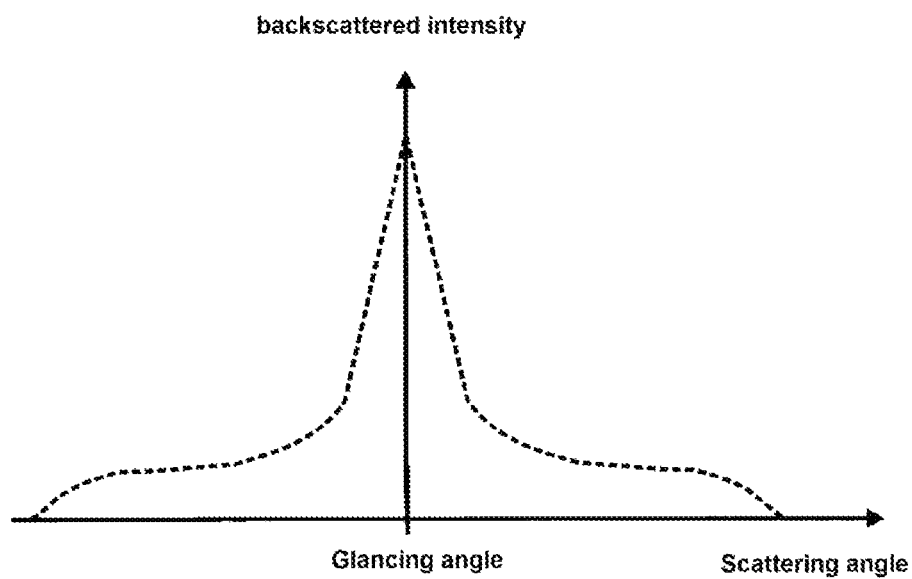
FIG. 1 depicts the intensity of the light portions backscattered by a boundary surface in the eye as a function of the scattering angle.
Figure 2:
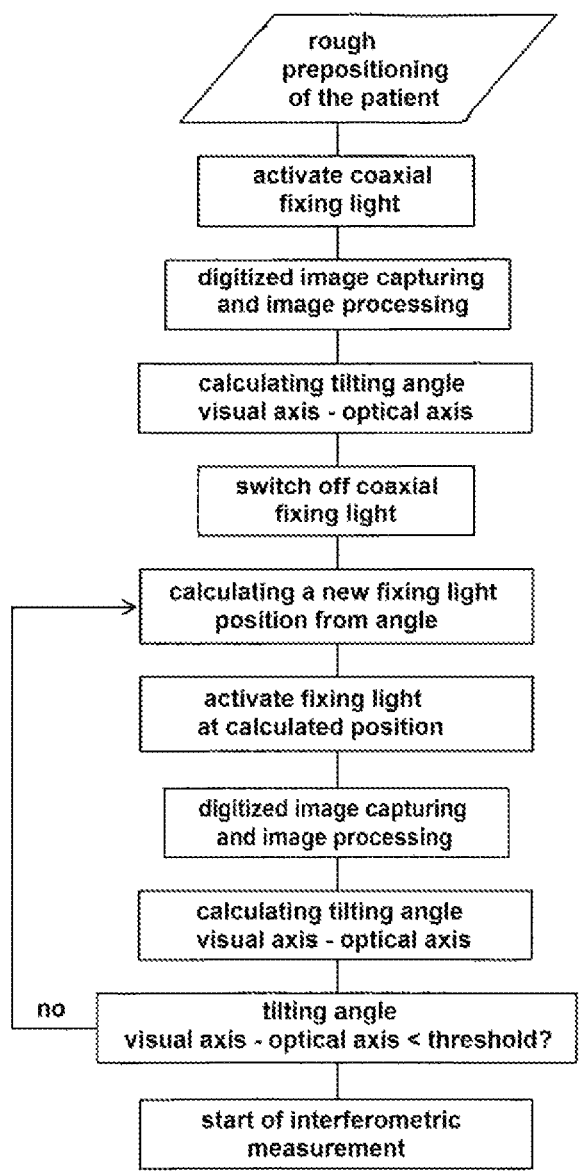
FIG. 2 depicts a flow diagram of the method according to the invention.

The method steps for automatic alignment are repeated until the determined angular deviation lies within the predefined tolerance. In this connection, a flow diagram of the method according to the invention is illustrated in FIG. 2.

After a "rough prepositioning of the patient", the "coaxial fixing mark is activated", imaged onto the eye, "captured as a digital image and analyzed" together with the eye, and "the tilting angle between the visual axis and the optical axis is calculated". Subsequently, the "coaxial fixing mark is deactivated", onto which fixing mark the patient had his/her eye fixed the whole time. Now, the position of a "corrected fixing mark is calculated" from the previously calculated tilting angle, and the "fixing mark is activated at the calculated position". The patient has to fix his/her eye again onto this corrected fixing mark. The fixing mark together with the eye is again "captured as a digital image and analyzed" and "the tilting angle between visual axis and optical axis is calculated". Subsequently, it is checked if the calculated "tilting angle is smaller than a predefined tolerance". If this is not the case (NO), the position of a "corrected fixing mark is calculated" again from the calculated tilting angle and the "fixing mark is activated at the calculated position", a "digital image is captured and analyzed", etc.

However, if this is the case (YES), i.e., the calculated tilting angle is smaller than the predefined tolerance, the "biometric measurement can be started".

If here the predefined tolerance is selected appropriately small, it can be ensured that the optical axis of the biometric measurement system coincides at least approximately with the optical axis of an eye. In the ideal case, in which in fact both axes coincide, the method would deliver optimal measurement signals.

The biometric measurement based on short-coherence interferometry is preferably carried out here in such a manner that the measuring light, on the one hand, is captured at least approximately in a diffraction-limited manner and, on the other, is superimposed with external reference light.

With a biometric measurement system that is automatically aligned in this manner, increased sensitivity can be achieved and, in addition, greater robustness and reliability can be ensured.

In a first example configuration of the method, the eye is illuminated by the fixing light source with a fixing mark in the visible spectral range. The image sensor for analyzing the reflex image can either detect the reflex of the fixing light or the reflex of an additional IR light source which can be arranged coaxially or, for example, annularly around the optical axis of the device. It is principally also possible to use the reflex image of the measuring light source for determining the angular deviation of the visual axis and the optical axis of the eye.

The defective vision of the patient's eye to be measured results in that the fixing mark is not sharply imaged on the eyeground and that, under certain circumstances, the patient has problems with fixing said fixing mark. Therefore, a second configuration of the method provides that for compensating the defective vision, the eye is illuminated by the fixing light source with an axially displaceable fixing mark. The amount required for the axial displacement can be found in the patient file and can be set on the biometric measurement system.

A third example configuration of the method considers the fact that the majority of the patients have an eye structure that deviates from the "ideal eye". Besides shortened or elongated eyes or a deformed cornea, lens and/or retina, a majority of the eyes of patients exhibit a tilting of the lens, which is in particular hindering during the measurement of the eye. Therefore, the method according to the invention provides to illuminate the eye by the fixing light source with a slightly laterally displaced fixing mark already at the beginning of the alignment. This has the advantage that the automatic alignment is accelerated due to the "elimination" of the illumination with a coaxial fixing mark. Here, the average tilting of the eye lens is 2°-5°.

In order to once again increase the reliability of the measured values obtained from the measuring beams reflected by the eye, it is advantageous to repeat the method steps A) to D) again, even if the determined angular deviation does not exceed the predefined tolerance.

During the actual determination of the different biometric parameters, i.e., after the completed alignment of the biometric measurement system, it is advantageous that the eye is illuminated by the measuring light source with a short-coherence measuring beam. The use of coherent radiation which, with regard to its spatial and temporal propagation has a fixed phase relationship, has established itself in ophthalmology, in particular for interferometric distance measurement of reflective materials. With this method, designated as optical coherence tomography (OCT), light of short coherence length is used with the aid of an interferometer for distance measurement. The advantage over competing methods is the relatively great penetration depth into scattering tissue and a high measuring speed while exhibiting a high axial resolution.

In a further example configuration of the method, the aperture is suitably reduced for the detection of the scattered light. This at least approximately diffraction-limited capture has the advantage that the measuring light obtained from the volume scattered light, which remits substantially uniformly in all directions, exhibits high spatial selectivity.

A final configuration of the method provides that the measuring light detected in a diffraction-limited manner is superimposed with external reference light. For this, the reference beam of the interferometer is decoupled beforehand and is not directed into the eye. As a result, the biometric measurement system is sensitive to potential movements of the patient's eye; however, only those light portions that actually include the depth information are superimposed with the reference beam.

The method according to the invention is characterized in that a variable fixing mark is used, the lateral position of which relative to the optical axis of the measurement arrangement is variably adjustable, and that the measuring light that is detected in an (approximately) diffraction-limited manner is superimposed with external reference light.

The device according to the invention for interferometrically determining various biometric parameters of an eye consists of an interferometric measuring arrangement, a measuring light source for illuminating an eye with measuring light, a fixing light source for illuminating the eye with a fixing mark, an image sensor for capturing the eye with the reflexes that arise, and an analysis unit for determining the angular deviation of the optical axis of the eye from the optical axis of the biometric measurement system.

Here, the fixing light source is designed such that the fixing mark to be generated is laterally displaceable. The volume scattered light primarily detected by an existing lens is superimposed as measuring light in the interferometric measuring arrangement with external reference light and is imaged on an existing measuring sensor. The analysis unit is capable of comparing the determined angular deviation with a predefined tolerance and, for the purpose of refixing as a result of said comparison, of having the fixing light source generate laterally displaced fixing marks on the basis of the calculated angular deviation, or of initiating the biometric measurement.

While the fixing light source is bound to emit light in the visible spectral range, the measuring light source emits a measuring beam in a spectral range that is not visible for the patient, which simplifies the analysis of the captured images significantly.

Figure 3:
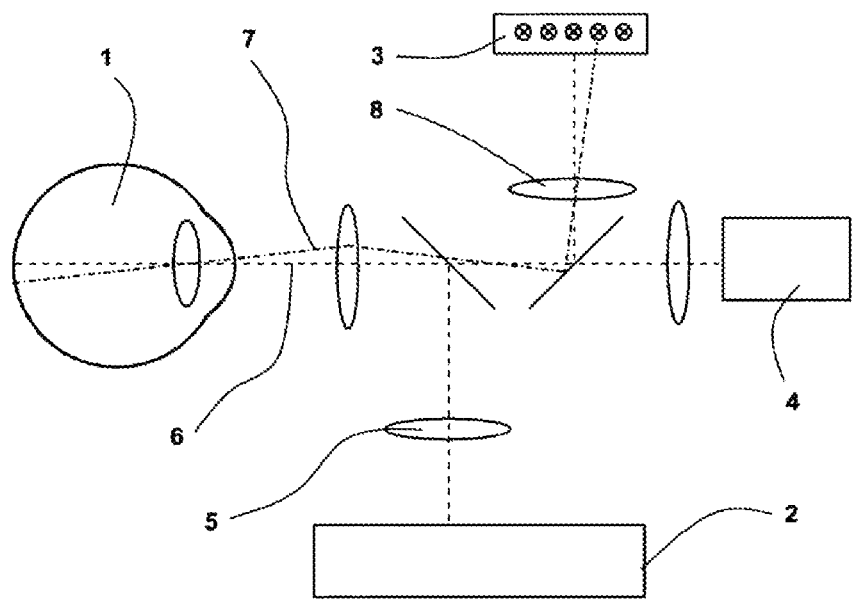
FIG. 3 depicts a schematic diagram of the device according to the invention.

In this connection, FIG. 3 shows a schematic diagram of the device according to the invention for determining various biometric parameters of an eye 1. The device consists of an interferometric measuring arrangement comprising a measuring light source and a measuring sensor 2, a fixing light source 3 with an imaging lens 8, an image sensor 4, a lens 5 for detecting volume scattered light, and an analysis unit (not illustrated). The illustration shows the aligned state in which the optical axes 6 of the eye and of the biometric measurement system are identical while the eye's 1 visual axis 7 characterized by the fixing light deviates therefrom.

The fixing light source is designed such that the fixing mark to be generated is laterally displaceable. Furthermore, there is a unit for generating a reduced detection aperture, and the interferometric measuring arrangement is designed for superimposing the measuring light with external reference light. Moreover, the analysis unit is capable of comparing the determined angular deviation with a predefined tolerance and, for refixing purposes as a result of said comparison, makes the fixing light source generate a laterally displaced fixing mark on the basis of the calculated angular deviation, or initiates the biometric measurement.

Here, determining the various biometric parameters is carried out only after alignment of the biometric measurement system. In detail, for the purpose of refixing, a laterally displaced fixing mark is generated by the fixing light source on the basis of the angular deviation calculated by the analysis unit, is imaged onto the eye and is captured by the image sensor with the reflexes that arise.

The analysis unit is capable of determining, from the position of the reflexes in relation to the center of the pupil or the iris, the angular deviation of the visual axis from the optical axis of the biometric measurement system and to compare it with a predefined tolerance. As a result of this comparison, in the event that the determined angular deviation exceeds a predefined tolerance, the fixing light source is prompted by the analysis unit to generate a laterally displaced fixing mark on the basis of the calculated angular deviation. Here, the alignment of the optical axis of the eye with the optical axis of the biometric measurement system is carried out by specifically changing the visual axis of the eye through a corrected fixing mark.

In the event that the determined angular deviation does not exceed a predefined tolerance, the determination of various biometric parameters of an eye is initiated by the analysis unit.

It is ensured here by the unit for generating a reduced detection aperture that the measuring light reflected by the eye can be detected in a diffraction-limited manner in the form of volume scattered light, can be superimposed in the interferometric measuring arrangement with external reference light, and can be imaged on the measuring sensor.

By application of the analysis unit, the interferometric measuring signals generated in this manner are analyzed and various biometric parameters of the eye are calculated.

If here the predefined tolerance is selected appropriately small, it can be ensured that the optical axis of the biometric measurement system virtually coincides with the optical axis of an eye and approximately optimal measuring signals are achieved.

The actual interferometric measurements for determining the position of optical boundary surfaces in the eye thus are carried out only after the biometric measurement system is adjusted to the physiology of the patient. This is preferably carried out automatically through the proposed solution, wherein the calculation and the activation of the fixing mark that is laterally displaced by the fixing light source is carried out automatically in the described manner and without involvement of the user.

The first advantageous configurations of the device refer to the fixing light source used. Preferably, a fixing light source is used by which fixing marks in the visible spectral range are generated. Furthermore, it is possible that the fixing light source is designed as an LC display, an array of light sources or as a laterally displaceable individual light source. However, it is also possible to arrange the fixing light source coaxially, for example, annularly, around the optical axis of the device.

On the other hand, defective vision of the patient's eye to be measured results in that the fixing mark is not sharply imaged on the eyeground and that, under certain circumstances, the patient has problems with fixing said fixing mark. Therefore, it is advantageous if the fixing light source, for compensating the defective vision, comprises a device for imaging an axially displaced fixing mark. The amount required for the axial displacement can be found in the patient file and can be set on the biometric measurement system.

As a device for imaging an axially displaced fixing mark, for example, imaging optics in the form of a zoom lens can be used. However, it is principally also possible that the device for imaging an axially displaced fixing mark is an actuator for axially displacing the fixing light source or an imaging lens.

In the light of the fact that the majority of the patients have an eye structure that deviates from the "ideal eye", wherein in addition to shortened or elongated eyes also a deformed cornea, lens and/or retina, or tilting of the lens can be found, it is possible with the proposed device to accelerate the alignment of the optical axis of the biometric measurement system with the optical axis of the eye.

For this purpose, the fixing light source is prompted to already generate at the beginning of the alignment a slightly laterally displaced fixing mark and to image it on the eye. This has the advantage that the automatic alignment is accelerated due to the "elimination" of the illumination with a coaxial fixing mark. Here, the average tilting of the eye lens is 2°-5°.

The second advantageous configurations refer to the measuring light source used. Preferably, the measuring light source is a measuring light source emitting a short-coherence measuring beam. The use of coherent radiation which, with regard to its spatial and temporal propagation, has a fixed phase relationship, has established itself in ophthalmology, in particular for interferometric distance measurement of reflective materials. With this method, designated as optical coherence tomography (OCT), light of short coherence length is used with the aid of an interferometer for distance measurement. The advantages over competing methods are the relatively great penetration depth into scattering tissue and a high measuring speed while exhibiting a high axial resolution.

The second advantageous configurations of the device refer to the unit used for generating a reduced detection aperture. This unit, for example, is an aperture or a single mode fiber. This at least approximate, diffraction-limited capture has the advantage that the measuring light obtained from the volume scattered light, which remits substantially uniformly in all directions, exhibits high spatial selectivity.

The measuring light captured in a diffraction-limited manner is superimposed in the interferometric measuring arrangement with external reference light. For this, the reference beam of the interferometer is decoupled beforehand and is not directed into the eye. As a result, the biometric measurement system is sensitive to potential movements of the patient's eye; however, only those light portions that actually include the depth information are superimposed with the reference beam.

The device according to the invention is characterized by the combination of a fixing light source for generating a laterally displaceable fixing mark, a unit for generating a reduced detection aperture, an interferometric measuring arrangement for superimposing the measuring light with external reference light, and an analysis unit that is capable of comparing the determined angular deviation with a predefined tolerance and, for the purpose of refixing as a result of said comparison, of having the fixing light source generate a laterally displaced fixing mark on the basis of the calculated angular deviation, or of initiating the biometric measurement.

With the method according to the invention and the device suitable for said method, a solution for interferometrically determining various parameters of an eye is made available, which solution delivers accurate and reliable measured values but nevertheless is not dependent on a highly accurate alignment of the device with the eye of a patient. Here, a sufficiently accurate alignment of the optical axis of an interferometric measuring arrangement with regard to the optical axis of an eye is preferably carried out automatically, wherein tilting or lateral displacements of the patient's eye and also the defective vision thereof can be considered during the alignment.

The present invention relates to a solution for interferometrically determining biometric parameters of an eye, wherein the optical axis of the biometric measurement system is aligned with the optical axis of an eye and ideally coincides with said axis.

The biometric measurement on the basis of short-coherence interferometry is preferably carried out here such that, on the one hand, the measuring light is captured at least in an approximately diffraction-limited manner and, on the other, is superimposed with external reference light.

With a biometric measurement system that is automatically aligned in this manner, increased sensitivity can be achieved and, in addition, greater robustness and reliability can be ensured.

The invention claimed is:

1. A method for interferometrically determining various biometric parameters of an eye, the method comprising:
   illuminating the eye with a measuring beam from a measurement light source and with a fixation light source with a fixation mark;
   capturing an image of the eye with an image sensor with reflections that arise;
   determining from a position of the reflections with regard to a center of a pupil or an iris, an angular deviation of an optical axis of the eye from an optical axis of a biometric measuring system by an analysis unit;
   wherein, prior to the determination of the various biometric parameters, alignment of the biometric measuring system is carried out, by the method further comprising:
      A) for refixation purposes, illuminating the eye by the fixation light source with a laterally displaced fixation mark based on the determined angular deviation,
      B) capturing another image of the eye with the image sensor with the reflections that arise,
      C) determining from the position of the reflections with regard to the center of the pupil or the iris, the angular deviation of the optical axis of the eye from the optical axis of the biometric measuring system by the analysis unit,
      D) comparing the determined angular deviation by the analysis unit with a predefined tolerance, and
      E) repeating method steps A) to D) if the determined angular deviation exceeds a predefined tolerance, and
   wherein determining various biometric parameters of the eye is carried out by the method further comprising
      F) detecting measuring light reflected by the eye in the form of volume scattered light,
      G) superimposing the measuring light as a quasi-diffraction-limited measuring beam with an external reference beam directed onto the measurement sensor, and
      H) analyzing the interferometric measurement signals with the analysis unit.

2. The method according to claim 1, further comprising illuminating the eye with infrared light from the fixation light source.

3. The method according to claim 1, further comprising, for compensating for defective vision, illuminating the eye by the fixation light source with an axially displaced fixation mark.

4. The method according to claim 1, further comprising laterally displacing the fixation mark of the fixation light source at the beginning of the alignment in consideration of an average tilting of the eye lens of 2-5°.

5. The method according to claim 1, further comprising capturing the image of the eye with the reflections that arise with a position-sensitive image sensor.

6. The method according to claim 1, further comprising repeating the method steps A) to D) again for increasing the reliability of the measured values obtained from the measuring beam reflected by the eye.

7. The method according to claim 1, further comprising illuminating the eye with the measuring light source with a short-coherence measuring beam.

8. The method according to claim 1, further comprising detecting primarily volume scattered light by a lens.

9. The method according to claim 1, further comprising decoupling the external reference beam of the interferometer beforehand and not directing the external reference beam into the eye.

10. A device for interferometrically determining various biometric parameters of an eye, said device comprising:
- an interferometric measuring arrangement;
- a measuring light source that illuminates the eye with measuring light;
- a fixation light source that illuminates the eye with a fixation mark;
- an image sensor that captures an image of the eye with reflections that arise; and
- an analysis unit that determines the angular deviation of the optical axis of the eye from the optical axis of the biometric measurement system;
- wherein the fixation light source is designed such that the fixation mark generated is laterally displaceable;
- an existing lens is designed such that primarily volume scattered light is detected;
- the interferometric measuring arrangement superimposes the measuring light with an external reference light and comprises a measuring sensor; and
- the analysis unit compares the determined angular deviation with a predefined tolerance and, for the purpose of refixation as a result of said comparison, makes the fixation light source generate a laterally displaced fixation mark on the basis of the calculated angular deviation, or initiates the biometric measurement.

11. The device according to claim 10, wherein the fixation light source comprises a fixation light source generating an infrared fixation mark.

12. The device according to claim 10, wherein the fixation light source comprises an LC display and an array of light sources or a laterally displaceable individual light source.

13. The device according to claim 10, wherein the fixation light source comprises a device that images an axially displaced fixation mark.

14. The device according to claim 13, wherein the device that images an axially displaced fixation mark comprises an imaging lens in the form of a zoom lens.

15. The device according to claim 13, wherein the device that images an axially displaced fixation mark comprises an actuator that axially displaces the fixation light source or an imaging lens.

16. The device according to claim 10, wherein the image sensor that captures an image of the eye with the reflections that arise comprises a position-sensitive image sensor.

17. The device according to claim 10, wherein the measuring light source comprises a measuring light source emitting a short-coherence measuring beam.

18. The device according to claim 10, wherein the lens for detecting volume scattered light comprises a single mode fiber.

* * * * *